United States Patent [19]

Elbe et al.

[11] Patent Number: 4,767,864

[45] Date of Patent: Aug. 30, 1988

[54] PROCESS FOR THE PREPARATION OF NITROMETHYLENE DERIVATIVES

[75] Inventors: Hans-Ludwig Elbe, Wuppertal; Bernd Baasner, Leverkusen, both of Fed. Rep. of Germany

[73] Assignee: Bayer Aktiengesellschaft, Leverkusen, Fed. Rep. of Germany

[21] Appl. No.: 2,837

[22] Filed: Jan. 13, 1987

[30] Foreign Application Priority Data

Feb. 1, 1986 [DE] Fed. Rep. of Germany ....... 3603100

[51] Int. Cl.$^4$ ............................................ C07D 401/08
[52] U.S. Cl. .................... 546/278; 544/333; 540/553
[58] Field of Search ............... 546/278; 544/333; 540/553

[56] References Cited

U.S. PATENT DOCUMENTS 4,002,765  1/1977  Tieman et al. ..................... 548/353

FOREIGN PATENT DOCUMENTS 135803   4/1985  European Pat. Off. .
163855  12/1985  European Pat. Off. .

OTHER PUBLICATIONS

Rudolf Gompper and Hartmann Schaefer, "Beitrage zur Chemie der Dithiocarbonsaureester und Ketenmercaptale", *Chem. Ber.*, 100, p. 591 (1967).

*Primary Examiner*—Jane T. Fan
*Attorney, Agent, or Firm*—Sprung Horn Kramer & Woods

[57] ABSTRACT

A process for the preparation of a nitromethylene derivative of the formula (I)

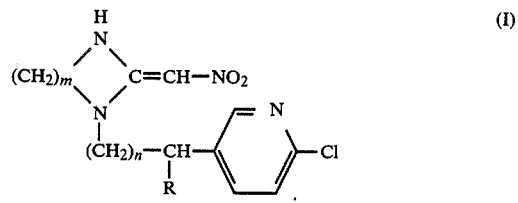

in which
R represents hydrogen or lower alkyl,
m represents the numbers 2, 3 or 4, and
n represents the numbers 0, 1, 2 or 3, comprising reacting a diamine of the formula (II),

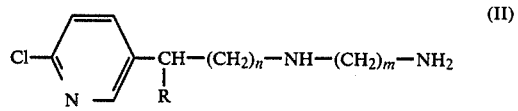

in which
R, m and n have the abovementioned meanings, with a fluoronitroethane derivative of the formula (IV)

$$CFX^1X^2-CH_2-NO_2 \qquad (IV)$$

in which
$X^1$ and $X^2$, independently of one another, represent fluorine or chlorine, in the presence of a base and if appropriate in the presence of a diluent, at temperatures between −10° C. and +100° C. The nitromethylene derivatives have insecticidal properties.

15 Claims, No Drawings

PROCESS FOR THE PREPARATION OF NITROMETHYLENE DERIVATIVES

BACKGROUND OF THE INVENTION

1. Field of the Invention

The present invention relates to a new process for the preparation of nitromethylene derivatives which have insecticidal properties.

2. Background Information

It has already been disclosed that nitromethylene derivatives of the formula (I)

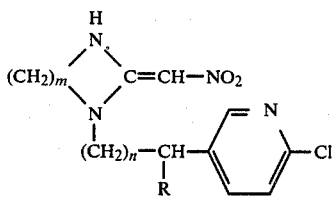

in which
R represents hydrogen or lower alkyl,
m represents the numbers 2, 3 or 4, and
n represents the numbers 0, 1, 2 or 3,
are obtained when compounds of the formula (II),

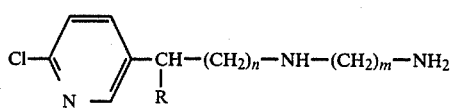

in which
R, m and n have the abovementioned meanings, are reacted with compounds of the formula (III),

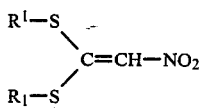

in which
$R^1$ represents lower alkyl or benzyl, or both $R^2$ groups together represent an alkylene group having at least 2 carbon atoms,
in the presence of an inert organic solvent, such as, for example, an alcohol or ether, at temperatures between 0° C. and 100° C. (cf. European Published Specification No. 163,855).

However, the disadvantage in this process is that the starting materials of the formula (III) must be prepared from nitromethane and carbon disulphide (cf. *Chem. Berichte*, 100, p. 591 [1967]).

Nitromethane is a generally known explosive having a high shock sensitivity. Carbon disulphide has a very low flashpoint of −20° C. and a relatively low ignition temperature of +120° C. Industrial use of these two starting materials would necessitate extensive and costly safety measures, for which reason the industrial value of this process is very limited.

A further disadvantage of the process is the cleavage of strongly smelling mercaptans during the reaction of the compounds of the formula (II) with those of the formula (III).

The reaction of 1-aminoalkanethiols with 2,2,2-trihalogeno-1-nitroethane derivatives to produce nitromethylene group-containing 1,3-thiazolidines, 1,3-thiazines and 1,3-thiazepines is known. In this connection see European Patent Specification No. 0,135,803 A2. However, 1-aminoalkanethiols which are significantly more reactive than the diamines were employed in this reaction.

SUMMARY OF THE INVENTION

It has now been found that known nitromethylene derivatives of the formula (I),

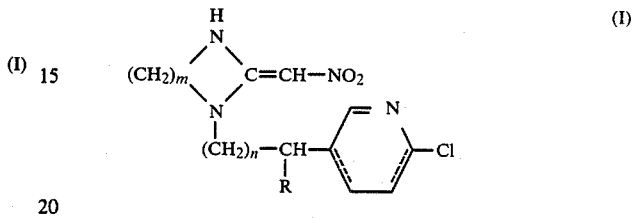

in which
R represents hydrogen or lower alkyl,
m represents numbers 2, 3 or 4, and
n represents numbers 0, 1, 2 or 3,
are obtained when diamines of the formula (II),

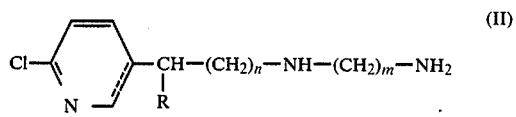

in which
R, m and n have the abovementioned meaning, are reacted with fluoronitroethane derivatives of the formula (IV)

in which
$X^1$ and $X^2$, independently of one another, represent fluorine or chlorine,
in the presence of a base and if appropriate in the presence of a diluent, at temperatures between −10° C. and +100° C.

DETAILED DESCRIPTION OF THE INVENTION

It is extremely surprising that the reaction according to the invention proceeds smoothly and in good yield under the process conditions stated. In spite of the generally described low reactivity of fluorine-substituted alkane derivatives, it was not expected that the fluoronitroethane derivatives of the formula (IV) would react so smoothly with the diamines of the formula (II) (cf., in this connection, for example, *J. Chem. Soc.*, 1954, p. 923: *J. Chem. Soc.*, 1951, p. 2495 and *Dokl. Akad. Nauk. SSSR*, 133, p. 933 [1960] [Engl.]).

The process according to the invention is distinguished by a series of advantages. Thus, it enables the preparation of nitromethylene derivatives of the formula (I) in good yields, easily accessible and easily handled compounds being employed as starting compounds. Furthermore, the reaction can be carried out simply, and the isolation of the final products presents no difficulties. The process according to the invention is therefore particularly suited for the preparation of nitromethylene derivatives of the formula (I) on an industrial scale.

If, for example, N-[2-(2-chloro-5-pyridyl)-1-propyl]-ethylenediamine and 1,1,1-trifluoro-2-nitro-ethane are used as starting materials, then the course of the process according to the invention can be illustrated by the following equation:

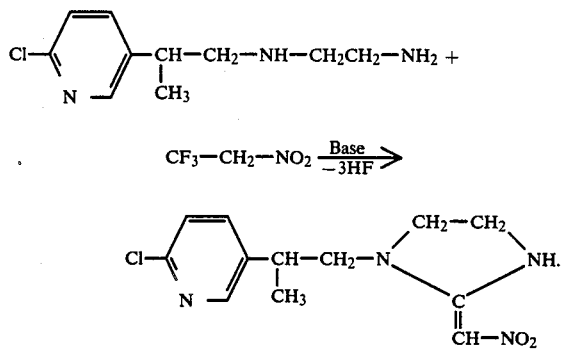

The diamines to be used as the starting materials in the process according to the invention are generally defined by the formula (II). In this formula, R preferably represents hydrogen, methyl, ethyl, propyl, isopropyl and n-(iso, sec.- or tert.-)butyl. The index m preferably represents the numbers 2, 3 or 4, and the index n preferably represents the numbers 0, 1, 2 or 3.

Particularly preferred starting materials are those diamines of the formula (II) in which R represents hydrogen, methyl or isopropyl.

The diamines of the formula (II) are known (cf. European Published Specification No. 163,855) and can be obtained by the processes stated therein, such as, for example, by reaction of pyridine derivatives of the formula (V)

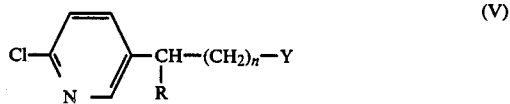

in which
R and n have the abovementioned meaning and
Y represents halogen or the —OSO$_2$Y' group, where Y' represents lower alkyl or represents aryl, with diamines of the formula (VI)

in which
m has the abovementioned meaning.

The fluoronitroethane derivatives which are additionally to be used as starting materials for the process according to the invention are generally defined by the formula (IV). In this formula, X$^1$ and X$^2$, independently of one another, preferably represent fluorine or chlorine.

The fluoronitroethane derivatives of the formula (IV) are known (cf., in this connection, EP-OS (European Published Specification) No. 101,133 and EP-OS (European Published Specification) No. 101,134). They are obtained by conjugated nitrofluorination of appropriate (V) according to the following equation:

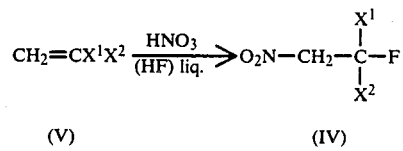

The process according to the invention is carried out in the presence of a base. All conventional inorganic and organic bases can be employed as a base. Sodium methylate, potassium methylate, sodium ethylate, potassium ethylate, sodium hydroxide, potassium hydroxide, sodium carbonate, potassium carbonate, calcium hydroxide and magnesium hydroxide are preferred.

The process according to the invention is, if appropriate, carried out in the presence of a diluent which is inert under the reaction conditions. These preferably include alcohols, such as methanol, ethanol, propanol, isopropanol, n-butanol or tert.-butanol; aliphatic and aromatic hydrocarbons, such as cyclohexane, benzene or toluene; ethers, such as diisopropyl ether, tetrahydrofuran or dioxane; halogenated hydrocarbons, such as 1,2-dichloroethane; and also acetonitrile, dimethylformamide, dimethyl sulphoxide and water.

The reaction temperatures can be varied within a relatively wide range on carrying out the process according to the invention. In general, the process is carried out at temperatures between $-10°$ C. and $+100°$ C., preferably at $0°$ C. to $50°$ C.

On carrying out the process according to the invention, 1 to 2 mol, preferably 1 to 1.5 mol of fluoronitroethane derivative of the formula (IV) and 3 to 6 mol, preferably 3 to 4.5 mol, of base are employed per mol of diamine of the formula (II). The reaction time is 1 to 12 hours, preferably 1 to 6 hours. The nitromethylene derivatives of the formula (I) are isolated in a conventional fashion.

The nitromethylene derivatives of the formula (I) which can be prepared by the process according to the invention are known (cf. European Published Specification No. 163,855). They are distinguished by very good insecticidal properties.

The process according to the invention is illustrated by the following non-limiting examples:

EXAMPLE 1

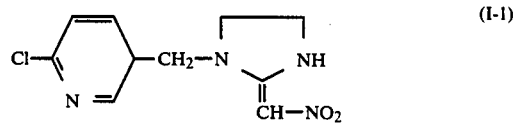

5 g (26.9 mmol) of N-(2-chloro-5-pyridylmethyl-)ethylene-diamine and 4.57 g (84.6 mmol) of sodium methylate are placed in 40 ml of methanol. A solution of 4.57 g (28.2 mol) of 1,1,1-dichlorofluoro-2-nitroethane in 20 ml of methanol is added dropwise at 5° C. to 10° C. within 30 minutes. After the addition is complete, the mixture is stirred for 5 hours at 20° C. The mixture is then concentrated by removal of the solvent by distillation in vacuo, and the residue is taken up in methylene chloride, washed with a small amount of water, dried, concentrated and recrystallized from methanol. 4.9 g (71.5% of theory) of 1-(2-chloro-5-pyridylmethyl)-2-(nitromethylene)-imidazoline a melting point of 160° C. to 161° C. are obtained.

EXAMPLE 2

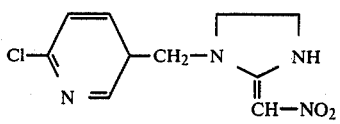 (I-1)

5 g (26.9 mmol) of N-(2-chloro-5-pyridylmethyl)ethylene-diamine and 11.7 g (84.6 mmol) of potassium carbonate are placed in 40 ml of methanol.

5 g (26.9 mmol) of N-(2-chloro-5-pyridylmethyl)ethylene-diamine and 11.7 g (84.6 mmol) of potassium carbonate are placed in 40 ml of methanol. A solution of 3.64 g (28.2 mmol) of 1,1,1-trifluoro-2-nitro-ethane in 20 ml of methanol is added dropwise at 5° C. to 10° C. within 30 minutes. After the addition is complete, the mixture is stirred for 5 hours at 20° C. The mixture is then concentrated by removal of the solvent by distillation in vacuo, and the residue is taken up in methylene chloride, washed with a small amount of water, dried, concentrated and recrystallized from methanol. 4.6 g (70.1% of theory) of 1-(2-chloro-5-pyridylmethyl)-2-(nitromethylene)-imidazoline of a melting point of 160° C. to 161° C. are obtained.

It will be appreciated that the instant specification and claims are set forth by way of illustration and not limitation, and that various modifications and changes may be made without departing from the spirit and scope of the present invention.

What is claimed is:

1. A process for the preparation of a nitromethylene derivative of the formula (I)

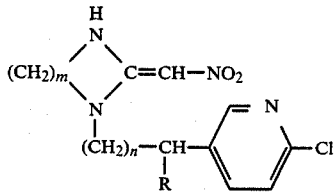 (I)

in which
R represents hydrogen or lower alkyl,
m represents the numbers 2, 3 or 4, and
n represents the numbers 0, 1, 2 or 3, comprising reacting a diamine of the formula (II),

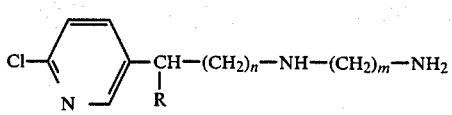 (II)

in which
R, m and n have the abovementioned meanings, with a fluoronitroethane derivative of the formula (IV)

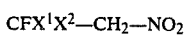

$CFX^1X^2-CH_2-NO_2$ (IV)

in which $X^1$ and $X^2$, independently of one another, represent fluorine or chlorine, in the presence of a base at temperatures between −10° C. and +100° C.

2. A process according to claim 1, which further comprises conducting the process in the presence of a diluent.

3. A process according to claim 1, wherein the base is selected from the group consisting of sodium methylate, postassium methylate, sodium ethylate, potassium ethylate, sodium hydroxide, postassium carbonate, calcium hydroxide and magnesium hydroxide.

4. A process according to claim 2, wherein the diluent is selected from the group consisting of alcohols, aliphatic hydrocarbons, aromatic hydrocarbons, ethers, halogenated hydrocarbons, acetonitrile, dimethylformamide, dimethyl sulphoxide and water.

5. A process according to claim 2, wherein the diluent is selected from the group consisting of methanol, ethanol, propanol, isopropanol, n-butanol, tert.-butanol, cyclohexane, benzene, toluene, diisopropyl ether, tetrahydrofuran, dioxane, acetonitrile, dimethylformamide, dimethyl sulphoxide and water.

6. A process according to claim 2, wherein the diluent is 1,2-dichloroethane.

7. A process according to claim 1, wherein the temperature range is from 0° C. to 50° C.

8. A process according to claim 1, wherein 1 to 2 mol of the fluoronitroethane derivative and 3 to 6 mol of the base are employed per mol of the diamine.

9. A process according to claim 1, wherein 1 to 1.5 mol of the fluoronitroethane derivative and 3 to 4.5 mol of the base are employed per mol of the diamine.

10. A process according to claim 1 for the preparation of a compound of the formula

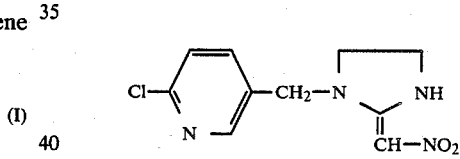

wherein the diamine is N-(2-chloro-5-pyridyl-methyl)-ethyllene-diamine and wherein the fluoronitroethane derivative is 1,1,1-dichlorofluoro-2-nitroethane.

11. A process according to claim 1 for the preparation of a compound of the formula

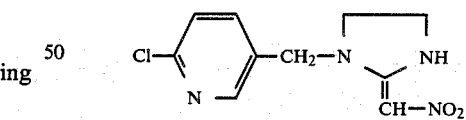

wherein the diamine is N-(2-chloro-5-pyridyl-methyl)-ethyllene-diamine and wherein the fluoronitroethane derivative is 1,1,1-trifluoro-2-nitroethane.

12. A process according to claim 1, wherein R is a lower alkyl selected from the group consisting of methyl, ethyl propyl, isopropyl, n-iso-butyl, n-sec.-butyl and n-tert.-butyl.

13. A process according to claim 1, wherein R is hydrogen, methyl or isopropyl.

14. A process according to claim 1, wherein the process is conducted for a time between 1 to 12 hours.

15. A process according to claim 1, wherein the process is conducted from a time between 1 to 6 hours.

* * * * *

UNITED STATES PATENT AND TRADEMARK OFFICE
CERTIFICATE OF CORRECTION

PATENT NO. : 4,767,864
DATED : August 30, 1988
INVENTOR(S) : Hans-Ludwig Elbe, et al It is certified that error appears in the above-identified patent and that said Letters Patent is hereby corrected as shown below:

Col. 2, line 19      Delete " ⌣ " and substitute -- ⌣ --

Col. 2, line 30      Delete " $\underset{N}{\smile}$ " and substitute -- $\underset{N}{\smile}$ --

Signed and Sealed this

Twenty-eighth Day of March, 1989

Attest:

DONALD J. QUIGG

*Attesting Officer*      *Commissioner of Patents and Trademarks*